(12) United States Patent
Feenstra

(10) Patent No.: US 6,921,500 B1
(45) Date of Patent: Jul. 26, 2005

(54) METHOD FOR MAKING A DENTAL ELEMENT

(75) Inventor: Frits Kornelis Feenstra, Pijnacker (NL)

(73) Assignee: Nederlandse Organisatie voor toegepast-natuurwetenschappelijk Onderzoek TNO, Delft (NL)

( * ) Notice: Subject to any disclaimer, the term of this patent is extended or adjusted under 35 U.S.C. 154(b) by 435 days.

(21) Appl. No.: 10/069,330

(22) PCT Filed: Aug. 24, 2000

(86) PCT No.: PCT/NL00/00586

§ 371 (c)(1),
(2), (4) Date: May 14, 2002

(87) PCT Pub. No.: WO01/13815

PCT Pub. Date: Mar. 1, 2001

(30) Foreign Application Priority Data

Aug. 24, 1999 (NL) .............................................. 1012897

(51) Int. Cl.⁷ ........................ B29C 41/22; A61C 13/20
(52) U.S. Cl. ........................ 264/19; 264/113; 264/162; 264/255; 264/308; 264/401; 264/409; 264/603
(58) Field of Search ................................ 264/400, 401, 264/482, 16–19, 255, 409, 603, 43, 162, 308

(56) References Cited

U.S. PATENT DOCUMENTS

| 5,204,055 A | * | 4/1993 | Sachs et al. .................... 419/2 |
| 5,658,412 A | * | 8/1997 | Retallick et al. .......... 156/272.8 |
| 5,690,490 A | | 11/1997 | Cannon et al. |
| 5,823,778 A | * | 10/1998 | Schmitt et al. .............. 433/214 |
| 5,900,207 A | * | 5/1999 | Danforth et al. ............. 264/603 |
| 5,902,441 A | | 5/1999 | Bredt et al. |
| 6,322,728 B1 | * | 11/2001 | Brodkin et al. ................ 264/19 |

FOREIGN PATENT DOCUMENTS

| EP | 0 431 924 A3 | 11/1991 |
| EP | 0 431 924 A2 | 12/1991 |
| WO | WO 91/03988 | 4/1991 |
| WO | WO 98/51747 | 11/1998 |

* cited by examiner

Primary Examiner—Stefan Staicovici
(74) Attorney, Agent, or Firm—Muserlian, Lucas & Mercanti, LLP

(57) ABSTRACT

The present invention relates to a method for fabricating a functional dental element, such as a crown. According to the invention, use is made of a three-dimensional printing technique. The major advantages of the invention are that no mold is needed anymore, which entails a considerable saving of costs, that a great accuracy is achieved, and that the element can be made of different materials.

12 Claims, No Drawings

METHOD FOR MAKING A DENTAL ELEMENT

The invention relates to a method for making a functional dental element and to a dental element obtainable by such method.

Dental elements, such as crowns, are used in clinical practice mainly for replacing or correcting dental structures. This can involve partly or wholly lost teeth or molars. To date, materials for such elements have been examined in particular for technological/physical and chemical properties. Currently, in addition, the biological aspect plays an increasing role.

Dental elements can be fabricated from different materials. Examples include polymers, metals, composites, combinations of porcelain and metal, porcelain and other ceramic materials. Glass and ceramic materials form an ideal group of materials for dental elements, because they are hard, have a high wear resistance, are chemically inert in many media (biocompatibility), and can be simply formed into an aesthetic dental element. A broad application of these materials, however, is impeded by the inherent brittleness which is often the result of limitations in the fabricating process and of the material choice. Recent developments have led to different ceramic systems, such as sintered ceramic, glass-infiltrated ceramic and glass-ceramic of various compositions, which are less brittle.

The fabrication of dental elements in practice is a complex and time consuming affair. The products involved are fabricated on an individual basis since the exact form of the element is different for every tooth or molar in every individual. Conventional techniques that have been used often utilize a mold. Since this mold can typically be used only once, it will be clear that these techniques are very costly.

In the past, techniques have been proposed which supposedly enable simplification of the fabricating process of dental elements. Thus, Abe et al., in Int. J. Japan Soc. Prec. Eng., vol. 30, no. 3, 1996, pp. 278–279, have proposed to carry out a selective laser sintering (SLS) with titanium. This technique, however, often gives rise to shrinkage. Also, microcracks may be formed, which renders the technique unsuitable for the fabrication of functional dental elements. In European patent application 0 311 214 it has been proposed to make a crown by milling. Milling does not provide the possibility of making colored elements. Moreover, the choice of suitable materials that can be processed by milling is limited. As noted, ceramic materials form an ideal group of materials for fabricating dental elements, because they are hard, highly wear-resistant and inert under many conditions.

U.S. Pat. No. 5,690,490 describes a method for the fabrication of a concept model for a dental element by so-called pinhead molding. The method concerns the use of a kind of matrix printing technique, whereby material is sprayed on. The printer is controlled with a CAD/CAM program. The data which this program utilizes have been obtained from a laser scan of the tooth or the molar to be replaced.

In U.S. Pat. No. 5,823,778, a method is described for fabricating a dental element whereby an impression of the teeth of a patient is obtained, which is subsequently used as a mold to make a copy of a dental element. This element is broken down in layers and each layer is scanned to obtain a three-dimensional computer model of the dental element.

One object of the present invention is to provide a technique whereby functional dental elements can be fabricated in a flexible and efficient manner. Another object is for the technique not to utilize a mold, and to enable making dental elements of polymeric, metallic or ceramic material, or of combinations thereof.

Surprisingly, it has presently been found that the stated objects are achieved by fabricating a dental element utilizing a three-dimensional printing technique.

Three-dimensional printing techniques are known per se, and described inter alia in European patent application 0 431 924, U.S. Pat. No. 5,902,441 and international patent applications 94/19112, 97/26302 and 98/51747. For a description of the details of the technique, reference is made to the documents mentioned, which are therefore to be understood to be inserted herein.

The method according to the invention is in principle suitable for fabricating all types of dental elements. Examples include crowns (front and lateral teeth), inlays, overlays, onlays, partial crowns, fixations and veneers.

Preferably, in a patient in whom a dental element is to be replaced/placed, it is first accurately measured what shape the element is to have. Often, if possible, the starting point will be the shape of the tooth or molar, or the portion thereof that is to be replaced. It is preferred that measurement can take place in a manner which causes the patient as little inconvenience as possible. Particularly suitable techniques for measuring the shape for the dental element make use of optical scan techniques, in particular lasers. In electronic form, data about the desired shape and dimensions are thereby obtained, which can be directly visualized in a computer. The electronic data about the shape and dimensions of the dental element are preferably used by a computer to control the execution of the three-dimensional printing technique. Another suitable method for measuring is by the CEREC-technique, Sirona Dental Systems GmbH, Bensheim, Germany.

In the three-dimensional printing technique, a suitable material is applied successively in layers, while specific steps are taken to ensure that each layer adheres to the preceding layer only at particular desired points. These specific steps are determined by the desired shape of the dental element and preferably controlled by the above-mentioned electronic data.

According to the invention, in the specific steps mentioned, use is made of a selective curing. The dental element is built up from layers, this time of a specific curable material, whereby each layer adheres to the desired positions of the preceding layer by allowing the material to cure only at the desired positions. The non-cured material will not adhere to the preceding layer and can be readily removed.

The curable material is preferably a nanomeric material, as described in WO-A-98/51747. Such a material consists of nanomeric, inorganic solid particles having polymerizable and/or polycondensable organic groups at their surface. It is preferred that this material is applied in the form of a flowable mass, for instance a dispersion of the material in water, an organic solvent, or a monomeric solution. In this context, a monomer solution is understood to mean a mixture of UV photopolymerizable monomers and a solvent suitable therefor. Suitable examples of monomers contain epoxy and/or acryl groups. As solvent, for instance styrene can be used. Nanomeric inorganic solid particles are understood to be particles having an average particle size (diameter) of less than 200 nm, preferably less than 100 nm. Found to be particularly suitable are particles having an average diameter of 5–50 nm.

The nanomeric, inorganic solid particles can consist of different materials, but it is preferred that they comprise a metal or metal compound. Examples of suitable materials are inter alia ZnO, CdO, $SiO_2$, $TiO_2$, $ZrO_2$, $CeO_2$, $SnO_2$, $Al_2O_3$, $In_2O_8$, $La_2O_3$, $Fe_2O_8$, $Cu_2O$, $Ta_2O_5$, $Nb_2O_5$, $V_2O_6$, $MoO_3$, $WO_3$, CdS, ZnS, PbS, $Ag_2S$, GaSe, CdSe, ZnSe, ZnTe, CdTe, AgCl, AgBr, AgI, CuCl, CuBr, $CdI_2$, $PbI_2$, $CdC_2$, SiC, AlAs, GaAs, GeAs, InSb, BN, AlN, $Si_3N_4$, $Ti_3N_4$, GaP, InP, $Zn_3P_2$, $Cd_3P_2$, phosphates, silicates, zirconates, aluminates, stannates and corresponding mixed oxides (as with a perovskite structure, e.g. $BaTiO_3$ and $PbTiO_3$). Preferred are materials comprising oxides, sulfides, selenides or tellurides of metals, or mixtures thereof. Preferred in particular are nanomeric particles of $SiO_2$, $TiO_2$, $ZrO_2$, ZnO, $Ta_2O_5$, $SnO_2$ and $Al_2O_3$ (in all forms, in particular as boehmite, AlO(OH)) and mixtures thereof.

The polymerizable and/or polycondensable organic groups can preferably form polymers under the influence of irradiation with a laser. This polymerization can proceed via any suitable mechanism. Preferably, the polymerization is photochemical or thermal. If desired, an initiator can be added to the flowable mass, being the form in which the nanomeric material is processed. (Meth)acryl, allyl, vinyl, epoxy, hydroxy, carboxy and amino groups are preferred, a particular preference being expressed for (meth)acryl and epoxy groups.

According to the invention, it is preferred that the polymerizable and/or polycondensable organic groups have a relatively low molecular weight. Preferably, their molecular weight is below 500, more preferably below 200.

The preparation of nanomeric, inorganic solid particles with polymerizable and/or polycondensable organic groups at their surface is known per se and described, inter alia, in international patent application 98/51747.

As mentioned, the nanomeric material is applied in the form of a flowable mass in layers. The flowable mass can be formed by forming a dispersion of the nanomeric material in water or any other suitable solvent. Here, it is preferred to work with a concentration between 25 and 60% by weight of nanomeric material, based on the weight of the dispersion. Applying the layers can be done in any suitable manner, such as spraying, streaking and the like. The thickness of the layers in these cases is preferably between 0.01 and 0.1 mm.

Between the application of the successive different layers, each layer is cured at specific, desired positions. The electronic data which have been obtained by measuring the shape and dimensions of the desired dental element in a patient can be used to control a laser which accurately irradiates each layer at the desired positions, so that the desired curing occurs and the layer adheres to a preceding layer at the desired points. Material which has not cured can be easily removed.

This method can also, as a special feature, process UV curing nanomer-containing resins which have been colored (with inorganic colorant), which enables the fabrication of colored functional dental elements. This process also provides the possibility of illuminating, and thereby curing, the surface in one go using a UV lamp, which proceeds faster than local curing with a laser. The process utilizes a number of nozzles equal to a power of 2, preferably between 100 and 10,000 nozzles, in particular 1536 nozzles. According to an alternative embodiment, the flowable mass can be applied in layers using an inkjet method. Preferably, use is made here of a piezo inkjet printer with a head of preferably 1536 nozzles. In this case, the thickness of the layers is preferably between 10 and 40 $\mu m$.

In particular cases, it has been found to be advantageous to subject the dental element to a thermal post-treatment, so that a complete curing is achieved. Thus, preferably, the dental element is briefly heated to a temperature between 60 and 150° C., more preferably between 80 and 130° C.

Instead thereof, or supplemental thereto, preferably a thermal densification is accomplished. To that end, the dental element is heated to a temperature of at least 250° C., preferably at least 400° C. and more preferably at least 500° C. This treatment contributes to the dental element obtaining particularly favorable properties.

When by one of the procedures described above the dental element has been formed, it may happen that it still needs to be additionally shaped to some extent. As has already been indicated, it is an advantage of the invention that it enables work to be done very accurately. Additional shaping will therefore be less laborious than in the techniques used heretofore. Ways in which additional shaping can be carried out include inter alia grinding, filing, polishing, sanding, blasting or treatment with a ball bed, depending on the selected material of the dental element. After this, typically a surface treatment/sealing is desirable.

The invention will presently be elucidated in and by the following examples.

Example 1

$ZrO_2$ particles of an average diameter of 10 nm are dispersed in isopropanol with stirring and ultrasound treatment. To modify the surface of the particles, 3.2 wt. %, based on the $ZrO_2$ content, of 3-methacryloxypropyltrimethoxysilane (MPTS) is added. The dispersion is stirred at 50° C. for 3 hours to obtain a silanized surface.

Subsequently, 3.2 wt. %, based on the $ZrO_2$ content, of tetraethyleneglycoldimethacrylate (TEGDMA) is added and stirring is done at 20° C. for 15 minutes. Three mole % of Irgacure® 184 is added per mole of double bond. Then the solvent is partly removed under vacuum.

Of the material thus obtained, the curing depth (Cd) is determined. An amount of the material is brought into a cylindrical form, which form transmits UV radiation. A UV dryer having a power of 400 $mW/cm^2$ is used for curing. The material is exposed to radiation for a period between 1 and 2 minutes (up to 20 UV radiation cycles). The power used is varied. The results of this tunnel curing test are programmed into an SLA machine (SLA250 of the firm 3D Systems Inc., Valencia Calif. USA).

Of the above-described dispersion, a layer of a thickness of 0.05 mm is applied to a building surface (20×20 cm) using a doctor blade. This layer is selectively irradiated with a HeCd laser, so that at specific points a curing reaction is initiated. This procedure is repeated until an element of the desired shape and dimension has been obtained. Finally, the element is exposed to a heat treatment at 120° C. for 15 minutes.

What is claimed is:

1. A method for fabricating a functional dental element using a three-dimensional printing technique, comprising:

applying successive layers of a flowable mass of a curable, nanomeric material onto each other using an inkjet method, and bonding between the layers by curing the curable, nonomeric material with UV light.

2. A method according to claim 1, wherein the shape and dimensions of the dental element are measured in a patient while using an optical scan technique.

3. A method according to claim 2, wherein the optical scan technique yields data about shape and dimensions in electronic form.

4. A method according to claim 1, wherein the layers are successively applied onto each other with selective curing, such that each layer adheres at desired positions to a preceding layer, and excess, non-adhering material can be removed.

5. A method according to claim 4, wherein the nanomeric material consists of nanomeric, inorganic solid particles with polymerizable and/or polycondensable organic groups at their surface.

6. A method according to claim 4, wherein the layers are applied using a piezo inkjet printer.

7. A method according to claim 4, wherein a computer is used for controlling, on the basis of the data obtained upon measuring, a laser which cures the nanomeric material at specific, desired positions by irradiation.

8. A method according to claim 4, wherein the dental element is exposed to a thermal post-treatment at a temperature of 60 to 150° C.

9. A method according to claim 4, wherein the dental element is thermally densified at a temperature of at least 250° C.

10. A method according to claim 1, wherein the dental element is additionally shaped by grinding, filing, polishing, sanding, blasting or treatment with a ball bed.

11. A method according to claim 2, wherein the optical scan technique is a laser technique.

12. The method of claim 1, wherein the flowable mass further includes a colorant.

* * * * *